United States Patent [19]

Janick et al.

[11] Patent Number: 4,615,141
[45] Date of Patent: Oct. 7, 1986

[54] PROCESS FOR ENCAPSULATING ASEXUAL PLANT EMBRYOS

[75] Inventors: Jules Janick; Sherry L. Kitto, both of West Lafayette, Ind.

[73] Assignee: Purdue Research Foundation, West Lafayette, Ind.

[21] Appl. No.: 640,923

[22] Filed: Aug. 14, 1984

[51] Int. Cl.⁴ .................................... A01C 1/06
[52] U.S. Cl. ............................ 47/57.6; 435/240; 435/948
[58] Field of Search ............... 47/58, 57.6; 435/240

[56] References Cited

FOREIGN PATENT DOCUMENTS 107141 10/1982 European Pat. Off. .

OTHER PUBLICATIONS

Synthetic Seed Technology, Rogers, Newsweek, Nov. 28, 1983, p. 111.

Janick, J. and Kitto, S. L., *HortScience*, 15(3), 107 (1980).
Janick, J. and Kitto, S. L., *HortScience*, 16(3), 88 (1981).
Janick, J. and Kitto, S. L., *HortScience*, 17(3), 60 (1982).
Janick, J. and Kitto, S. L., *HortScience*, 18(4), 104 (1983).

*Primary Examiner*—Robert E. Bagwill
*Attorney, Agent, or Firm*—Barnes & Thornburg

[57] ABSTRACT

Synthetic seeds are produced by encapsulating asexual plant embryos with a nontoxic, biocompatible, water-soluble coating material. The encapsulation is effected by mixing asexual embryos with a synthetic coating material, dispensing such mixture as droplets onto a sterile surface, and drying such droplets to constant weight at room temperature to form detachable wafers consisting of one or more asexual embryos embedded in the synthetic coating material.

21 Claims, 1 Drawing Figure

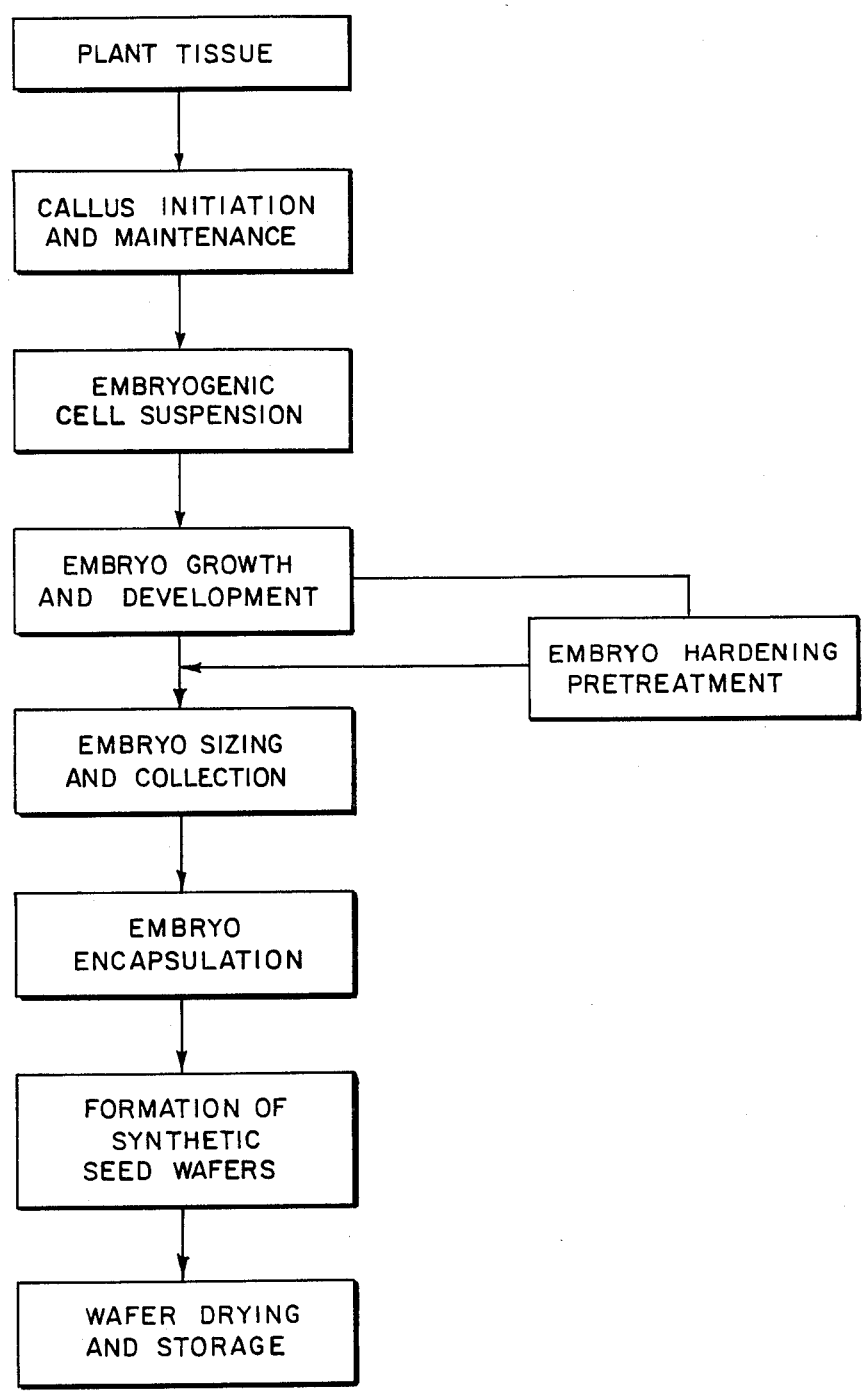

PROCESS FOR ENCAPSULATING ASEXUAL PLANT EMBRYOS

BACKGROUND OF THE INVENTION

This invention relates to the production of synthetic seeds. It particularly relates to the encapsulation of asexual embryos with an artificial seed coat effective to maintain viability of the embryo and to permit germination with normal seedling development.

Seeds are normally produced by growing plants as a direct consequence of the sexual process. The normal sexual seed consists of a partially developed embryo in a resting phase, as well as various seed coats and nutritive tissues necessary for transport, food storage, and protection. Such seeds are usually the result of the sexual process, having an association with floral parts and requiring pollination.

The production of artificial seeds by asexual means would have substantial benefits for the seed industry and agriculture, particularly in connection with hybrid plants. A cell from almost any part of a plant can produce an asexual embryo and from it another entire plant which is virtually identical to the original plant. Such asexual reproduction of cross-pollinating plants by seed would essentially eliminate the circuitous hybrid route required for maintaining uniformity and hybrid vigor. This is particularly useful for those species for which conventional hybridization techniques are difficult. Asexual seed reproduction could also serve as a delivery system for genetically-engineered genotypes produced by in vitro techniques. Artificial seeds could be produced year round and in very little space.

Asexual embryogenesis in vivo is a well known phenomenon particurlarly in the Rutaceae, Cactaceae, Celastraceae, Liliaceae, Myrtaceae, Orchidaceae, Rosaceae, and Solanaceae families. Tisserat, et al. *Horticultural Reviews, pp.* 1–99 (1979). The production of asexual embryos by in vitro techniques has also been widely reported. Al-Abta et al. *Ann. Bot.*, 42, 773–782 (1978); Ammirato, P.V. *Bot. Gaz.*, 135, 328–337 (1974); Litz, et al. *Hort Science*, 15, 733–735 (1980); McWilliams, et al. *Ann. Bot.*, 38, 243–250 (1974); Mullins et al. *Expt. Bot.*, 27, 1022–1030 (1976); Sangwan et al. *Expt. Bot.*, 26, 868–881 (1975). In vitro-produced asexual embryos differ from in vivo-produced seeds by the absence of seed coats. In the present invention, in virtro-produced asexual embryos can be converted into "seeds" by providing a suitable synthetic seed coat that maintains seed viability and permits germination of the seed.

A method for encapsulating seed embryos has been reported in *Newsweek*, Nov. 28, 1983, p. 111. The method described therein involves a two-step process for coating a pregerminated embryo. The embryo is first coated with a gelatinous material, calcium alginate, then with an extremely thin layer of biodegradable polymer to prevent the coated seeds from sticking together. This encapsulation technology does not produce a true artificial "seed" because the embryo is pregerminated prior to encapsulation. The method of the invention described herein does form a true "seed" because a nongerminated or quiescent embryo is encapsulated within an artificial seed coat. This is accomplished by encapsulation with a non-toxic, biocompatible, water-soluble coating material in a one-step process.

It is, therefore, an object of the present invention to produce artificial seeds having an asexual embryo encapsulated in an artificial seed coat.

Another object is to provide a method to produce mature embryos via asexual embryogenesis without precocious germination.

It is a further object to provide a synthetic seed coat which will prevent lethal desiccation of the embryo, maintain viability of the seed embryo, dissolve in water, and permit germination of the seed.

Yet another object is to increase the survival rate of the encapsulated embryo.

Other objects of the present invention will be apparent from the following description and claims.

SUMMARY OF THE INVENTION

It has now been discovered that synthetic seeds can be produced by encapsulating asexual plant embryos with a synthetic seed coat. Asexual plant embryos are obtained by asexual embryogenesis techniques well known in the art. Embryo hardening methods may be employed during the embryo induction phase to improve embryo survival rate following encapsulation. Such pretreated or untreated embryos are thereafter contacted with a non-toxic, biocompatible, water-soluble coating material to form a mixture of embryos suspended in the said coating material. The resulting mixture is dispensed as droplets onto a sterile, non-adhering surface and dried to constant weight under aseptic conditions to form synthetic seeds or wafers consisting of one or more embryos embedded in the coating material. Such synthetic seeds can be stored and germinated at a later date to produce plants that are virtually identical to the plants from which they orginate.

DESCRIPTION OF THE DRAWING

The drawing illustrates a typical protocol for producing synthetic seeds wherein asexual embryos are grown in tissue culture, encapsulated with a synthetic coating material, and dried to form synthetic seeds or wafers. Embryos can be hardened during the induction stage using one or more hardening methods more fully described herein.

DETAILED DESCRIPTION OF THE INVENTION

In accordance with the present invention, artificial seeds are produced according to the general procedure illustrated in the drawing. Asexual embryos are produced from plant tissue in accordance with known in vitro somatic embryogenesis techniques. Somatic embryogenesis is the formation of embryos from somatic cells, rather than directly via the zygote. Somatic cells include any ordinary plant tissue, i.e., any tissue following the first division of the embryo. Such cells are induced to become "somatic embryos" by synthetic plant hormones. Thus a cell from virtually any part of a plant can produce an embryo and from it another entire plant which is a replica or clone of the original.

In vitro asexual embryogenesis has been demonstrated for many plants, including carrot, corn, celery, ginseng, caraway, orchard grass, triploid plantains, grapevine, *Carica stipulata, Medicago sativa, Antirrhinum majus, Pennisetum americanum*. McWilliam, et al. *Ann. Bot.*, 38, 243–250 (1974); Al-Abta, et al. *Ann. Bot.*, 42, 773–782 (1978); Chang, et al. *Theor. Appl. Genet.*, 57, 133–135 (1980) Ammirato, et al. *Bot Gaz*; 135, 328–337 (1974); Conger, et al. *Science*, 221, 850–851 (1983);

Cronhauer, et al. *Plant Cell Reports*, 2, 289–291 (1983); Litz, et al. *HortScience*, 15(6), 733–735 (1983); Lupotto, *Pflanzenphysiol*, 111, 95–104 (1983); Mullins, et al. *J. Expt. Bot.*, 27, 1022–1030 (1976); Sangivan, et al. *J. Expt. Bot.*, 26, 868–881; Vasil, *Amer. J. Bot.*, 69(9), 1441–1449 (1982). Although the occurrence of somatic embryogenesis has been demonstrated in vitro for mature tissues, in most cases, somatic embryogenesis is more likely to occur in less mature tissues extending as far back as the embryo and nucellar tissue.

During the embryo induction phase, the embryos can be hardened, i.e. induced to resist environmental stress, by methods hereinafter described. Such hardening methods render asexual embryos quiescent, thereby increasing the survival rate of the embryos following encapsulation. Suitable hardening methods useful in the invention comprise exposing the embryos during the embryo induction phase to high inoculum density, high sucrose concentrations, chilling, and/or exposure to abscisic acid (ABA).

Asexual embryos, thus obtained, with or without hardening pretreatment, are thereafter encapsulated with a coating material hereinafter described. The coating material dries to form a thin, non-toxic film enclosing one or more embryos, protecting the embryos during storage but readily redissolving in an aqueous solution. Representative coating materials useful in the invention to encapsulate asexual embryos comprise water soluble resins such as polyethylene oxides having a molecular weight ranging from about 100,000 to about 500,000, acrylic copolymers containing carboxyl groups, starch and synthetic polymers of acrylamide and sodium acrylate, synthetic trioctahedral smectite, synthetic sodium magnesium lithium silicate, potassium propenoate acrylamide copolymers, hydroxy-ethylcellulose, methylcellulose, gelatins, starches, and the like.

Referring now to the drawing, in the practice of this invention, asexual embryos are proliferated in tissue culture according to the following general procedures. Callus is obtained from plant tissue and inoculated into fresh liquid culture media containing nutrients and plant hormones to form cell suspension capable of forming embryos. Embryo growth is initiated by placing such cell suspension into another liquid, hormone-free medium for further growth and development. The resulting embryogenic suspension containing cells, cell aggregates, callus clumps, and embryos of varying maturity is recultured every three days. Such embryo proliferation techniques are more fully described hereinafter.

Callus can be initiated from virtually any plant tissue using techniques such as those described in Dougall, *Plant Cell and Tissue Culture Manual*, W. Alton Jones Cell Science Center, Lake Placid, N.Y., p. 6.21 (1978). The tissue cells quickly cease behaving like the particular plant tissue from which they originate and form callus. The callus is subsequently grown in darkness at 25° C. and recultured every four to eight weeks onto gelled medium, containing medium addenda common to tissue culture, such as pyridoxine hydrochloride, thiamine hydrochloride, nicotinic acid, myo-inositol, sucrose, agar, Murashige and Skoog salts (Murashige,; Skoog, *Physiol. Plant.*, 15, 473–497 (1962)), as well as synthetic plant hormones comprising auxins such as dichlorophenoxyacetic acid (2,4-D), and cytokinins such as 6-furfurylaminopurine (Kinetin) and the like.

Cell suspensions can thereafter be initiated from callus tissue using techniques such as those described in Gamborg, *Nat. Res. Coun. of Can.*, pp. 7–8 (1975), in media typically containing the same plant nutrients and hormones as described above. Cell aggregates having a cell aggregate size of about 0.45 micrometer and preferably a cell aggregate size of about 0.15 mm to about 1.00 mm are inoculated into such medium at a density of about 0.2 g/25 ml. Cell suspensions are recultured every 14 days into fresh cell suspension medium.

Embryo growth can thereafter be maximized for the purpose of the present invention by inoculating aggregates of 14-day-old, stationary-phase cell suspension ranging in size up to above about 1.00 mm at a density ranging from about 0.2 g/25 ml to about 1.6 g/25 ml, and preferably at a density of about 0.4 g/25 ml into a hormone-free liquid medium. The resulting liquid cultures are grown at a temperature ranging from about 25° C. to about 30° C., preferably at a temperature of about 29° C., on a gyratory shaker revolving at about 120 rpm, with exposure to a light source for about 16 hours out of 24 hours. The resulting embryogenic suspension containing cells, cell aggregates, callus clumps, and embryos of varying maturity are recultured every three days into fresh liquid medium during the embryo induction phase, typically lasting about one week to about three weeks.

Survival of encapsulated embryos can be increased by commingling embryo suspensions with abscisic acid (ABA) in a concentration ranging up to about $10^{-5}$ M, preferably about $10^{-7}$ M to about $10^{-6}$ M and optimally about $10^{-6}$ M, during the two-week embryo induction period. The ABA is filter sterilized prior to addition. Increased survival of ABA-treated embryos may be due to the imposition of a developmental arrest or a quiescence during which time embryos mature and become more resistant to desiccation.

A further increase in survival rate can be obtained by chilling asexual embryos to a temperature of about 0° C. to about 7° C., preferably about 4° C. Chilling is accomplished during the last three days of the 14-day induction growth cycle. Increased survival is obtained by chilling with or without ABA. Chilling plant tissue may mimic some effects of cold hardening that plants acquire outdoors as temperatures decrease in the fall such as, cessation of growth, accumulation of carbohydrate, and reduction of moisture content. An increased tolerance of the protoplasm to dehydration is associated with the reduction in intracellular water.

Embryos can also be hardened by increasing the sucrose concentration of the maintenance medium from a normal level of about 20 g/liter to above about 240 g/liter, preferably to about 120 g/liter, during the last three days of the two-week embryo induction phase. Such concentrations can be employed with or without ABA. Sucrose has a two-fold role in vitro acting as both a carbon source and an osmotic agent. Increased osmotic stress has been associated with cell plasmolysis, cell growth inhibition, and elevation of endogenous ABA levels when applied in vitro. Exposure of embryos to high sucrose has been linked to maturation, inhibition of precocious germination, and acquisition of desiccation tolerance. Drew, *Hort. Res.*, 19, 79–84 (1979); Ammirato, et al. *Bot. Gaz.*, 132, 149–158 (1971); Norstog, *Amer. J. Bot.*, 53, 613–614 (1966).

Yet another method for increasing embryo survival rate is to increase the denisty at which cell suspensions are inoculated into the embryogenic growth medium during the embryo induction phase. For this purpose, cell suspensions can be inoculated at a high inoculum density of about 0.4 g/25 ml or above. While the precise mechanism has not been established, high inoculum density is believed to influence embryo maturation by creating a favorable developmental environment that may be due to osmotic or hormonal factors.

One or more layers of coating material are thereafter applied to the untreated or pretreated asexual embryos. To achieve this result it is convenient to commingle the embryo suspension with an aqueous solution of the synthetic coating material in proportions sufficient to produce final artificial coating concentrations ranging from about 5.0 g/liter to about 50.0 g/liter, and preferably a concentration of about 25 g/liter. The mixture of embryo and coating material is dispensed in aliquots of up to about 0.3 ml, preferably about 0.2 ml, into a sterile non-adhering surface. Suitable non-adhering surfaces include teflon, polypropylene, polyethylene, and the like. The resulting droplets are dried to about constant weight at a temperature ranging from about 20° C. to about 30° C., preferably about 25° C., under aseptic conditions such as in a laminar flow hood. Such droplets dry to form detachable wafers consisting of asexual embryos encapsulated in a synthetic seed coat, the drying being continued for a time sufficient to allow the wafers to separate from the non-stick surface. The time necessary to form a dried, detachable synthetic seed wafer varies with temperature and humidity but is typically not less than 5 hours. The synthetic seed wafers thus obtained can thereafter be easily removed, stored, and separately planted.

The size of the embryo also affects the survivability of the synthetic seed wafers. Suspensions of larger embryos having a size ranging from about 0.39 mm to about 1.0 mm more easily survive encapsulation and wafer formation than smaller embryos.

The invention described herein utilizes inexpensive and readily available materials. In vitro culture has extended asexual embryogenesis to may plants; thus, there are many plant sources for initiating embryo cell cultures. Likewise, there are many sources of polymeric or gelatinous seed coating materials suitable for coating embryos. Polyethylene oxide is a suitable non-toxic, biocompatible, water-soluble coating material that is commercially available as POLYOX WSR N-750 water-soluble resin, manufactured by Union Carbide Corporation.

The following examples illustrate the application of the present invention to numerous embryogenic suspensions as well as hardening agents. These examples are given only for the purpose of illustration, and are not to be construed as limiting in any way.

EXAMPLE 1

Artificial seeds were produced by growing asexual embryos and encapsulating them with polyethylene oxide in the following manner.

Tissue cells were obtained from the secondary phloem of "White Belgium" carrot (*Daucus carota L.*) using the culturing methods described by Dougall. *Plant Cell and Tissue Culture Manual.* W. Alton Jones Cell Science Center, Lake Placid, N.Y., 1978, p. 6.21. Callus cells were then initiated by growing the phloem cells in darkness at 25° C. in the callus induction media shown in Table 1. The resulting callus cells were recultured every four to eight weeks onto fresh callus maintenance medium. See Table 1.

TABLE 1

Media for Growth and Embryogenesis of Carrot Cultures

| Component (Liter$^{-1}$) | Callus Induction | Callus Maintenance | Cell Suspension | Embryo Growth |
|---|---|---|---|---|
| Murashige and Skoog Salts (g) | 4.33 | 4.33 | 4.33 | 4.33 |
| Pyridoxine HCl (mg) | 0.5 | 0.5 | 0.5 | 0.5 |
| Thiamine HCl (mg) | 0.4 | 0.4 | 0.4 | 0.4 |
| Nicotinic acid (mg) | 0.5 | 0.5 | 0.5 | 0.5 |
| Myo-inositol (mg) | 100.0 | 100.0 | 100.0 | 100.0 |
| Sucrose (g) | 20.0 | 20.0 | 20.0 | 20.0 |
| Agar, Difco Bacto, (g) | 1.0 | 1.0 | 0.0 | 0.0 |
| 2,4-D (mg) | 1.0 | 0.1 | 0.1 | 0.0 |
| Kinetin (mg) | 0.2 | 0.2 | 0.2 | 0.0 |

The resulting callus cells were used for initiating cell suspensions, using the techniques of Gamborg in a medium containing synthetic plant hormones as shown in Table 1. Gamborg, o.l., *Nat. Res. Coun. Can.*, 7–8 (1975). For this purpose, callus cells ranging in size from 0.15 mm to 1.00 mm were inoculated into the cell suspension medium at a density of 0.2 g of cells per 25 ml of medium. The cell suspensions were recultured into fresh cell suspension medium every 14 days.

The formation of embryos was maximized by inoculating 14-day-old suspension of cells ranging in size from 0.15 mm to 1.00 mm into another, hormone-free liquid growth medium (Table 1) at a density of 0.4 g/25 ml. These liquid cultures were maintained on a gyratory shaker (120 rpm) at 29° C. for a photoperiod of 16 hours. Embryonic suspension was recultured every three days into fresh growth medium during a two-week embryo induction phase. All media were autoclaved for 30 minutes at 121 C. and 124 kPa prior to use.

Artificial seed coats were applied to embryos by mixing embryogenic suspensions ranging in size from 0.15 mm to 1.00 mm with an aqueous solution of POLYOX WSR N-750 water-soluble resin, manufactured by Union Carbide Corporation to produce final POLYOX resin concentrations of 5.0 g/l, 12.5 g/l, and 25 g/l.

The mixture of embryogenic suspension and polyethylene oxide coating material was dispensed as 0.2 ml droplets onto teflon sheets and dried at room temperature to constant weight in a laminar flow hood. The POLYOX resin dried to form a thin, detachable embryo-encapsulating film or wafer, thereby forming synthetic seeds containing one or more embryos. The time necessary to form a dried detachable wafer varied between four and six hours.

The viability of the encapsulated embryos was determined by dissolving the artificial seed coat and subjecting the embryos to a germination test according to the following procedure. Coated embryo wafers were resuspended (rehydrated) at their original culture density in fresh hormone-free embryogenic medium and agitated for about 14 hours to dissolve the synthetic seed coating material. The resulting rehydrated embryo suspensions were collected, cultured on moist filter paper supports in small Petri dishes (15×60 mm) containing 3 ml of medium, and grown for a period of two to three weeks at 25° C. and for a photoperiod of 16 hours per 24 hours. Embryo counts and growth measurements were taken after two to three weeks.

As shown in Table 2, the most effective POLYOX coating concentration was determined to be 25 g/l (2.5% (w/v)). Water-coated embryos, when tested as controls, did not survive drying.

The results of this study demonstrated that asexual embryos can be encapsulated with a water-soluble resin and survive disiccation. The most effective POLYOX concentration, 2.5% (w/v), was used in all subsequent encapsulation studies.

TABLE 2

Effect of POLYOX Concentration on Survival of 'White Belgium' Carrot Embryos

| Coating Material | | Drying Time (Hours) | No. Embryos/ 30 Wafers |
|---|---|---|---|
| None | | 0 | 4 |
| Water | | 4 | 0 |
| | | 5 | 0 |
| | | 6 | 0 |
| POLYOX | 0.5% | 4 | 2 |
| | | 5 | 0 |
| | | 6 | 0 |
| | 1.25% | 4 | 1 |
| | | 5 | 0 |
| | | 6 | 0 |
| | 2.5% | 4 | 4 |
| | | 5 | 2 |
| | | 6 | 2 |

EXAMPLE 2

The effect of drying synthetic seeds was determined for artificial carrot seeds. Embryogenic cell suspensions were initiated from a root of a carrot of undetermined species by a method generally similar to that of Example 1. Embryogenic suspensions were coated with 2.5% (w/v) POLYOX WSR N-750 and dried to constant weight at room temperature in a laminar flow hood. The moisture loss during the drying period was typically 90 to 98% of the total wafer weight, the drop in moisture content being greatest during the first two hours, and constant wafer weight being attained after four hours of air-drying.

The water-coated control embryos did not survive the drying step. POLYOX-coated embroys survived typical drying periods of four to eight hours. Some encapsulated embryos survived 32 hours of drying.

When wafers were oven dried at 75° C. for 24 hours to drive off any additional moisture, the additional moisture loss was 4% for non-coated control wafers and less than 1% for POLYOX-coated wafers. See Table 3. Thus, essentially all moisture loss occurred during the initial four hour drying period, producing synthetic seeds that were virtually as dry as natural seeds.

TABLE 3

Moisture Loss Comparison for Coated and Non-coated Seeds

| | Wafer Weight | | |
|---|---|---|---|
| Coating Treatment | Air-dried 32 Hours (mg) | Oven-dried 24 Hours, 75° C. (mg) | Percentage Moisture Loss |
| No POLYOX | 5.0 | 4.8 | 4 |
| 2.5% POLYOX | 11.0 | 10.9 | <1 |

EXAMPLE 3

Pretreating the embryogenic suspensions by contacting such suspensions with abscisic acid (ABA) increased the survival rate of encapsulated embryos.

Embryogenic cell suspensions were initiated from a root of a carrot of undetermined species by a procedure generally similar to that of Example 1. Such suspensions were pretreated with either $10^{-7}$ M or $10^{-6}$ M (ABA) during the two-week embryo induction phase. The resulting pretreated embryos were coated with 2.5% POLYOX. Embryo survival after drying was determined by redissolving wafers in embryogenic medium and culturing he rehydrated embryo suspension for three weeks as described in Example 1.

Initial embryo counts were made before POLYOX was added and final embryo counts were made after the three week growth period. See Table 4. The percent survival provided in parentheses in Table 4 is based on the initial embryo count. Pretreating the embryogenic suspension with $10^{-6}$ M ABA increased encapsulated embryo survival to 40% of the initial number of embryos, suggesting that ABA pretreatment increases survival of coated embryos.

The influence of the period of time at which embryos were pretreated with ABA was also examined. Embryo suspensions were treated with $10^{-6}$ M ABA during the first nine days, the entire 14 days, or the last six days of the embryo induction phase. ABA treatment appeared to be more effective at the end of the two week embryo induction phase.

TABLE 4

Effect of 14-day ABA Pretreatment and Encapsulation on Survival of Carrot Embryos

| ABA Concentration | Drying Time (Hours) | Initial Embryo Count[1] | Final Embryo Count[1] | |
|---|---|---|---|---|
| | | | No POLYOX | POLYOX 2.5% |
| No ABA | 5 | 102 | 0 | 10.3 ± 7 |
| | 6.5 | 102 | 0 | 3.3 ± 4 |
| $10^{-7}$ M ABA | 5 | 98 | 0 | 11.0 ± 10 |
| | 6.5 | 98 | 0 | 2.7 ± 0.6 |
| $10^{-6}$ M ABA | 5 | 78 | 0 | 21.0 ± 3 |
| | 6.5 | 78 | 0 | 31.7 ± 14 |

[1]Number of embryos per 10 wafers.

EXAMPLE 4

The effectiveness of embryo since size and ABA pretreatment on embryo survival was examined. Cell suspensions from the root of a carrot of undetermined species were initiated and maintained by a procedure generally similar to that of Example 1. These embryogenic cell suspensions, either untreated or pretreated with $10^{-6}$ M ABA, were separated into three size ranges: 0.15 to 0.27 mm, 0.27 to 0.39 mm, and 0.39 to 1.00 mm in diameter. An embryo suspension from each size range was resuspended in embryogenic medium at a density of 0.29 g/ml, encapsulated with 2.5% (w/v) POLYOX and dried for seven hours. The viability of the various seeds was tested by a procedure generally similar to that of Example 1.

Embryo suspensions pretreated with $10^{-6}$ M ABA were better able to survive POLYOX coating and seven hours of drying. See Table 5. The largest embryos had the greatest survival rate whether they were pretreated with ABA or not.

TABLE 5

Effect of Embryo Size and ABA Pretreatment on Embryo Survival After Encapsulation

| ABA Concentration | Initial Mean Embryo Size (mm) | Initial Embryo Count[1] | Final Embryo Count[1] |
|---|---|---|---|
| No ABA | 0.6 | 940 | 5.0 ± 3.7 |
| | 0.4 | 1140 | 0.8 ± 0.8 |

TABLE 5-continued

Effect of Embryo Size and ABA Pretreatment on Embryo Survival After Encapsulation

| ABA Concentration | Initial Mean Embryo Size (mm) | Initial Embryo Count[1] | Final Embryo Count[1] |
|---|---|---|---|
|  | 0.2 | 560 | 0.0 |
| $10^{-6}$ M ABA | 0.6 | 640 | 9.4 ± 7.5 |
|  | 0.4 | 888 | 1.2 ± 1.1 |
|  | 0.2 | 620 | 0.8 ± 0.8 |

[1]Number of embryos per 10 wafers.

EXAMPLE 5

The effectiveness of high inoculum density as an embryo hardening pretreatment method was examined. Asexual embryos of a carrot of undetermined species were initiated and maintained by a procedure generally similar to that of Example 1, with the exception that high inoculation density of 0.8 g/25 ml was employed during the embryo induction phase. Such inoculum densities were used alone or in combination with $10^{-6}$ M ABA during the 14-day embryo-induction phase. The embryos were dried for 11.5 hours in Experiment 1 and for 7 hours in Experiment 2.

Embryo suspension inoculated at 0.8 g/25 ml produced fewer embryos than at 0.4 g/25 ml. Encapsulated embryos grew after rehydration, indicating that the growth-retarding effect of the hardening treatment was reversible. Non-encapsulated embryos initiated at either density with or without ABA treatments did not survive drying. Either high inoculum density or ABA increased survival of encapsulated embryos. As shown in Table 6, the percent survival was as high as 51% for POLYOX-coated wafers inoculated at a density of 0.8 gl 25 ml. Survival of embryos receiving both high inoculum density and ABA was less than expected if the effect of the treatments had been additive.

TABLE 6

Survival of Asexual Embryos of Carrot Initiated at High Inoculum Density

| Inoculum Density | ABA Concentration | Initial Embryo Count[1] | Final Embryo Count[1] | |
|---|---|---|---|---|
|  |  |  | No POLYOX | POLYOX 2.5% |
| Experiment 1 |  |  |  |  |
| 0.4 g/25 ml | 0 | 2600 | 0 | 28 ± 15 |
|  | $10^{-6}$ | 1200 | 0 | 132 ± 38 |
| 0.8 g/25 ml | 0 | 760 | 0 | 127 ± 22 |
|  | $10^{-6}$ | 620 | 0 | 129 ± 27 |
| Experiment 2 |  |  |  |  |
| 0.4 g/25 ml | 0 | 930 | 0 | 212 ± 21 |
|  | $10^{-6}$ | 1150 | 0 | 499 ± 95 |
| 0.8 g/25 ml | 0 | 340 | 0 | 175 ± 21 |
|  | $10^{-6}$ | 320 | 0 | 85 ± 12 |

[1]Number of embryos per 10 wafers.

EXAMPLE 6

The effectiveness of high sucrose concentration as a hardening pretreatment method was demonstrated. Asexual embryos of a carrot of an undetermined species were initiated and maintained by a procedure generally similar to that of Example 1, except that the sucrose concentration of the growth medium was increased to 12% sucrose both with and without $10^{-6}$ M ABA being present in the embryogenic cell suspension. The resulting wafers were air-dried for six hours in Experiment 1 and for seven hours in Experiment 2.

Embryo suspensions grown in medium with 12% sucrose produced fewer embryos than did control suspensions grown with 2% sucrose. Yet the encapsulated embryos grew after rehydration, indicating that the growth-retarding effect of the hardening treatment was reversible.

Non-coated embryos of all treatments failed to survive drying. Survival of POLYOX-coated embryos was two to three times higher with 12% sucrose than with 2% surcrose without ABA. Survival of embryos grown with 2% sucrose was increased by ABA in both experiments 1 and 2, but survival was much higher in experiment 2 than in experiment 1. Survival of embryos initiated with both high sucrose and ABA was less than that of the untreated or control embryo suspension of experiment 1 and less than that of embryo suspension pretreated with $10^{-6}$ M ABA alone in experiment 2.

TABLE 7

Survival of Asexual Carrot Embryos Pretreated With High Sucrose Concentrations

| Hardening Pretreatment | Initial Embryo Count[1] | Final Embryo Count[1] | |
|---|---|---|---|
|  |  | No POLYOX | POLYOX 2.5% |
| EXPERIMENT 1 |  |  |  |
| No Treatment | 495 | 0 | 16 ± 11 |
| $10^{-6}$ M ABA | 381 | 0 | 16 ± 17 |
| 12% Sucrose | 392 | 0 | 42 ± 16 |
| $10^{-6}$ M ABA and 12% Sucrose | 333 | 0 | 7 ± 4 |
| EXPERIMENT 2 |  |  |  |
| No Treatment | 940 | 0 | 29 ± 5 |
| $10^{-6}$ M ABA | 400 | 0 | 232 ± 35 |
| 12% Sucrose | 900 | 0 | 57 ± 11 |
| $10^{-6}$ M ABA and 12% Sucrose | 610 | 0 | 99 ± 24 |

[1]Number of embryos per 10 wafers.

EXAMPLE 7

The effectiveness of chilling the embryo suspension during the embryo induction phase to increase embryo viability was demonstrated. Asexual embryos of a carrot of an undetermined species were initiated and maintained by a procedure generally similar to that of Example 1. The embryogenic suspensions were hardened by chilling to 4° C. during the last three days of the embryo induction phase. During the three day chilling period, cultures received constant light at 2.6 umol/sm[2] from tungsten lamps. ABA, when provided, was filter sterilized and added to the cooled medium. The resulting seed wafers were air dried for seven hours in both experiments.

The survival rates of chilled carrot embryos are given in Table 8. Embryo survival was increased markedly in both experiments and increased survival was obtained with or without ABA pretreatment.

TABLE 8

Survival of Asexual Embryos of Carrot Pretreated By Chilling to 4° C. During The Last Three Days of the Induction-Growth Cycle

| Hardening Pretreatment | ABA Concentration | Initial Embryo Count[1] | Final Embryo Count[1] | |
|---|---|---|---|---|
|  |  |  | No POLYOX | POLYOX 2.5% |
| EXPERIMENT 1 |  |  |  |  |
| No Chilling | No ABA | 630 | 0 | 8 ± 5 |
|  | $10^{-6}$ M ABA | 540 | 0 | 7 ± 3 |

TABLE 8-continued

Survival of Asexual Embryos of Carrot
Pretreated By Chilling to 4° C. During The
Last Three Days of the Induction-Growth Cycle

| Hardening Pretreatment | ABA Concentration | Initial Embryo Count[1] | Final Embryo Count[1] No POLYOX | POLYOX 2.5% |
|---|---|---|---|---|
| Chilling | No ABA | 487 | 0 | 140 ± 41 |
|  | $10^{-6}$ M ABA | 177 | 0 | 51 ± 31 |
| EXPERIMENT 2 |  |  |  |  |
| No Chilling | No ABA | 1220 | 0 | 3 ± 5 |
|  | $10^{-6}$ M ABA | 1160 | 0 | 3 ± 1 |
| Chilling | No ABA | 980 | 0 | 25 ± 5 |
|  | $10^{-6}$ M ABA | 680 | 0 | 54 ± 22 |

[1]Number of embryos per 10 wafers.

EXAMPLE 8

The effect of wafer storage on embryo viability was examined. Asexual embryos of a carrot from an undetermined species were initiated and grown by a procedure generally similar to that of Example 1. Embryogenic suspensions were pre-chilled to 4° C. during the last three days of the embryo-induction phase. POLYOX-coated wafers containing prechilled embryo suspension were dried for seven hours and were placed in Petri dishes and stored without light at 4° C. for various periods of time ranging from 0 to 98 hours. The storage times and survival rates are given in Table 9. Survival of encapsulated embryos generally declined with storae time, however, some embryos remained viable after 98 hours of storage.

In a second experiment, POLYOX-coated wafers containing embryo suspension were contacted with $10^{-6}$ M ABA, chilled during the last three days of embryo induction, and stored in darkness at either 26° C. or 4° C. for as long as 16 days. POLYOX-coated wafers survived up to four days storage at 26° C. and at least 16 days storage at 4° C. Embryo survival rates are given in Table 10.

TABLE 9

Survival of Prechilled, Encapsulated Carrot Embryos

| Storage at 4° C. (Hour) | Number of Embryos/14 Wafers |
|---|---|
| 0 | 35[1] |
| 24 | 2 |
| 36 | 3 |
| 48 | 8 |
| 74 | 1 |
| 98 | 1 |

TABLE 10

Survival of Encapsulated Carrot Embryos Pretreated With $10^{-6}$ M ABA and Chilling

| Storage (Days) | Number Embryos/20 Wafers 25° C. | 4° C. |
|---|---|---|
| 0 | 7[1] |  |
| 1 | 0 | 2 |
| 2 | 1 | 1 |
| 4 | 2 | 1 |
| 8 | 0 | 1 |
| 16 | 0 | 2 |

[1]Represents 1% survival from initial embryo count.

While we have described the invention with respect to specific materials, such materials are illustrative only. Numerous modifications and equivalents will be apparent to those of ordinary skill in this art without departing from the spirit of the invention.

What is claimed is:

1. A method for the production of synthetic seeds comprising:
    a. developing asexual plant embryos from somatic plant tissue,
    b. hardening such asexual embryos during their developement to induce resistance to environmental stress,
    c. coating such hardened asexual embryos with a solution of a non-toxic biocompatible, water-soluble synthetic coating material, and
    d. drying the resulting solution-coated embryos to provide viable embryos encapsulated in the coating material.

2. The method of claim 1 wherein such plant embryo is a carrot embryo.

3. The method of claim 1 wherein such plant embryo is a caraway embryo.

4. The method of claim 1 wherein such coating material is polyethylene oxide, having a molecular weight ranging from about 100,000 to about 500,000.

5. The method of claim 1 wherein such coating material is methylcellulose.

6. The method of claim 1 wherein such coating material is hydroxyethylcellulose.

7. The method of claim 1 wherein such coating material is an acrylic copolymer containing carboxyl groups.

8. The method of claim 1 wherein such coating material is a polymer of acrylamide and sodium acrylate.

9. The method of claim 1 wherein such coating material is synthetic trioctahedral smectite.

10. The method of claim 1 wherein such coating material is synthetic sodium magnesium lithium silicate.

11. The method of claim 1 wherein such coating material is a potassium propenoate acrylamide copolymer.

12. The method of claim 1 wherein such asexual plant embryos are hardened during embryo developement and prior to encapsulation by contacting the said embryos in suspension with about $10^{-6}$ M to about $10^{-7}$ M abscisic acid.

13. The method of claim 1 wherein such asexual plant embryos are hardened during embryo developement and prior to encapsulation by culturing such embryos at an inoculum density ranging from about 0.4 g to about 1.6 g of embryogenic cells per 25 ml of growth medium.

14. The method of claim 1 wherein such asexual embryos are hardened during embryo development and prior to encapsulation by culturing such embryos in a medium wherein sucrose is present in a concentration of about 20 to about 240 g of sucrose per liter of medium.

15. The method of claim 1 wherein such asexual embryos are hardened during embryo development and prior to encapsulation by chilling such embryos during the last three days of the embryo induction phase to a temperature ranging from about 0° C. to about 7° C.

16. A method for the production of synthetic seeds comprising:
    a. developing asexual plant embryos from somatic plant tissue,
    b. hardening such asexual embryos during their development to induce resistance to environmental stress,
    c. coating such hardened asexual embryos with a solution of a non-toxic biocompatible, water-soluble synthetic coating material, and d. drying the resulting solution-coated embryos to provide viable embryos encapsulated in the coating material, in which method the asexual embryos are encapsulated by mixing equal volumes of embryo suspension in growth medium with an aqueous solution of polyethylene oxide having a concentration of about 5 g per 100 ml, dispensing the mixture as droplets of about 0.2 ml onto a sterilized teflon surface and drying such droplets to constant weight in a laminar flow hood, whereby detachable wafers consisting of one or more embryos embedded in coating material are formed.

17. A method for encapsulating asexual embryos which comprises commingling a suspension thereof in a growth medium with a non-toxic, biocompatible, water-soluble coating material, dispensing the resulting mixture as droplets of up to about 3 ml onto a sterile, non-adherent surface, and drying the resulting droplets to constant weight at a temperature of about 10° C. to about 30° C., whereby detachable wafers consisting of one or more embryos embedded in such coating material are formed.

18. The method of claim 17 wherein such wafers are dried to constant weight in a laminar flow hood.

19. An artificial seed product comprising a hardened, quiescent, asexual plant embryo encapsulated in accordance with the method of claim 1, which, upon growth, yields a plant essentially identical to the plant from which the asexual plant embryo is developed.

20. The method of claim 1 wherein the asexual embryos are encapsulated in the coating material by (1) suspending the embryos in a solution of the coating material; (2) dispensing droplets of the resulting suspension onto a surface; and (3) drying the droplets to form wafers consisting of one or more embryos embedded in the coating material.

21. The method of claim 20 wherein the droplets are dried at a temperature of about 20° to about 30° C.

* * * * *

UNITED STATES PATENT AND TRADEMARK OFFICE
CERTIFICATE OF CORRECTION

PATENT NO. : 4,615,141

DATED : October 7, 1986

INVENTOR(S) : Jules Janick et al

It is certified that error appears in the above-identified patent and that said Letters Patent is hereby corrected as shown below:

Column 3, line 2, change "(1983)" to --(1980)--.

Column 5, line 39, change "may" to --many--.

Column 6, line 35, change "121  C." to --121° C.--.

Column 8, line 6, change "he" to --the--.

Column 8, line 40, delete "since".

Column 11, line 31, change "storae" to --storage--.

Signed and Sealed this

Twenty-fourth Day of February, 1987

Attest:

DONALD J. QUIGG

Attesting Officer     Commissioner of Patents and Trademarks